United States Patent
Welacky et al.

(10) Patent No.: US 6,407,038 B1
(45) Date of Patent: Jun. 18, 2002

(54) METHOD FOR CONTROLLING PLANT-PARASITIC NEMATODES

(75) Inventors: Thomas William Welacky, Kingsville; Edward Topp, London, both of (CA)

(73) Assignee: Her Majesty the Queen in right of Canada, as represented by c/o Minister of Agriculture and Agri-Food Canada, Harrow (CA)

( * ) Notice: Subject to any disclaimer, the term of this patent is extended or adjusted under 35 U.S.C. 154(b) by 0 days.

(21) Appl. No.: 09/594,764

(22) Filed: Jun. 16, 2000

Related U.S. Application Data

(60) Provisional application No. 60/211,212, filed on Jun. 13, 2000.

(51) Int. Cl.$^7$ .................. A01N 63/00; A01N 61/00; A01N 59/00; C05G 3/02; C05F 3/00
(52) U.S. Cl. .................. 504/102; 504/367; 424/543; 424/600; 424/677; 424/682; 424/687; 424/688; 424/694; 71/12
(58) Field of Search .................. 424/543, 600, 424/677, 682, 687, 688, 694; 71/DIG. 1, 12; 504/367, 102

(56) References Cited

U.S. PATENT DOCUMENTS

| | | | |
|---|---|---|---|
| 4,554,002 A | * | 11/1985 | Nicholson .................. 71/12 |
| 4,781,842 A | * | 11/1988 | Nicholson .................. 210/751 |
| 4,902,431 A | * | 2/1990 | Nicholson et al. |

OTHER PUBLICATIONS

CAB Abstract 75:59402, 1975.*
CAB Abstract 92: 34724, 1991.*
CAB Abstract 94: 119714, 1994.*
CAB Abstract 84 : 55511, 1984.*
Chemical Abstracts 123: 64848, 1995.*
Chemical Abstracts 107: 204585, 1987.*
Chemical Abstracts 130: 3402, 1997.*
CAB Abstracts 82: 61081, 1981.*
Hornick, S.B. et al., "Utilization of sewage sludge compost as a soil conditioner and fertilizer for plant growth," Agriculture Information Bulletin, Agricultural Research Service, USDA, No. 464, 1984, pp. 1–32.*
Habicht, William A., Jr., "The nematicidal effects of varied rates of raw and composted sewage sludge as soil organic amendments on a root–knot nematode,"0 Plant Disease Reporter, vol. 59(8), Aug. 1975, pp. 631–634.*
Hallquist, Soren, "Beneficial use of sewage sludge in the Gothenburg region, Sweden," Wager Science Technology, vol. 16(12), 1984, pp. 449–460.*

\* cited by examiner

*Primary Examiner*—John Pak
(74) *Attorney, Agent, or Firm*—Kenyon & Kenyon

(57) ABSTRACT

A method for controlling Tylenchid plant-parasitic nematodes through application of an effective amount of an alkaline-stabilized sludge is described. In accordance with particular embodiments, the alkaline-stabilized sludge may be applied to the plant, seed or locus thereof.

7 Claims, No Drawings

METHOD FOR CONTROLLING PLANT-PARASITIC NEMATODES

CROSS-REFERENCE TO RELATED APPLICATION

This application claims the benefit of U.S. Provisional Patent Application No. 60/211,212 titled "Method for Controlling Plant-Parasitic Namatodes," filed Jun. 13, 2000.

FIELD OF THE INVENTION

The present invention relates generally to the field of agricultural pest control, and in particular to a method for controlling plant-parasitic nematodes.

BACKGROUND OF THE INVENTION

A significant problem faced by the agricultural industry is reductions in crop yield due to the damaging effect of Tylenchid plant-parasitic nematodes on plant hosts. For example, soybeans are an important staple crop in the United States and elsewhere throughout the world. However, for nearly a century, soybean plants have been subject to infestation by the soybean cyst nematode, *Heterodera glycine* (hereinafter, "SCN"). SCN is a major pest to soybean growers, presenting significant eradication problems once it becomes established. Moreover, SCN can inflict serious crop damage, substantially reducing yield, even before any symptoms of infestation are visible aboveground. By the time such symptoms appear, the infestation is often quite severe and yields have likely suffered for a significant period of time. Indeed, it is not uncommon for a crop to have suffered a 25–75% loss in yield by the time visual symptoms are observed. Accordingly, there is a significant need for an effective method of controlling Tylenchid plant-parasitic nematodes.

SUMMARY OF THE INVENTION

The present invention is directed to methods for controlling Tylenchid plant-parasitic nematodes through application of an effective amount of an alkaline-stabilized sludge. In accordance with particular embodiments, the alkaline-stabilized sludge may be applied to the plant, seed or locus thereof.

DETAILED DESCRIPTION

The present invention is generally directed to methods for reducing the damaging effects of Tylenchid plant-parasitic nematodes on plant hosts. Methods in accordance with embodiments of the claimed invention are useful for suppressing Tylenchid plant-parasitic nematodes including, but not necessarily limited to, members of the genus Heterodera, which infect the host families Poaceae (e.g., oats, barley, rye, wheat, grasses), Umbelliferae (e.g., carrots), Fabaceae (e.g., Phaseolus spp., red and white clover, peas), Solanaceae (e.g., tobacco, tomatoes, potatoes), and Brassica (e.g., cabbage, canola); members of the genus Pratylinchus, which infect more than 350 hosts, including apple, cherry, and other fruit trees, tomatoes, potatoes, corn and sugar beets; and members of the genus Meloidogyne, which infect more than 700 hosts, including most cultivated crops and ornamentals.

In accordance with a particular embodiment, Tylenchid plant-parasitic nematodes are controlled through application of an effective amount of an alkaline-stabilized sludge to a plant host, seed or locus thereof. In accordance with particular implementations of this embodiment, the alkaline-stabilized sludge may be applied using any technique typically used for application of granular fertilizers or pesticides, including but not limited to broadcast-incorporation (e.g., applied substantially uniformly across the soil surface) and side-dressing (e.g., applied in a band or strip next to a crop row, usually in the middle of the row). Suitable rates of application may be as low as approximately 5 tons per acre or as high as approximately 20 tons per acre. A rate of approximately 5 tons per acre has been found to be particularly effective in controlling soybean cyst nematode (SCN).

An alkaline-stabilized sludge suitable for use in such embodiments may be prepared in accordance with processes disclosed in U.S. Pat. No. 4,554,002, issued Nov. 19, 1985 to John P. Nicholson and assigned to N-Viro Energy Systems Ltd. of Toledo, Ohio. In general, the N-Viro '002 Patent describes processes for preparing a disintegratable, friable product useful as a soil conditioner. In accordance with embodiments described therein, the product is made by treating wastewater sludge to reduce pathogens, and involves mixing the sludge with kiln dust (i.e., a byproduct of the cement and lime industries) to form a mixture of from about 1:9 to 3:7 kiln dust to wastewater sludge by weight, wherein the amount of kiln dust is sufficient to raise the pH of the mixture to at least 12 and to maintain such elevated pH for at least two hours while the mixture interacts.

As discussed in the N-Viro '002 Patent, the mixture of wastewater sludge and kiln dust produces a useful soil conditioner and partial fertilizer by eliminating or significantly reducing undesirable characteristics of each respective raw material. The mixture can be permitted to cure until it is sufficiently cohesive so that it can be readily formed into granulated particles by shredding, crushing or the like. The resultant product is friable, so that upon being spread on the ground and exposed to the elements (as in farming, for example) it will break down into small, fine particles.

Another suitable alkaline-stabilized sludge may be prepared in accordance with processes disclosed in U.S. Pat. No. 4,781,842, issued Nov. 1, 1988 to John P. Nicholson and also assigned to N-Viro Energy Systems, Ltd. In accordance with embodiments described in the N-Viro '842 Patent, an improved method for using cement kiln dust and other alkaline materials to treat waste sludge combines high pH (e.g., greater than about 12) and drying to pasteurize and stabilize the sludge.

Yet another suitable alkaline-stabilized sludge may be prepared in accordance with the processes disclosed in U.S. Pat. No. 4,902,431, issued Feb. 20, 1990 to John P. Nicholson et al. and assigned to N-Viro Energy Systems, Ltd. In accordance with embodiments disclosed in the N-Viro '431 Patent, an improved method for using alkaline materials to treat waste sludge combines high pH (e.g., greater than about 12), drying, and increased temperature (e.g., greater than about 50° C.) to pasteurize and stabilize the sludge. The N-Viro '431 Patent further shows that a wide range of alkaline materials, including coal combustion ashes, can be beneficially used in such processes.

The foregoing discussion of suitable alkaline-stabilized sludges is provided by way of example only, as alkaline-stabilized sludge produced from other processes may also be used in accordance with embodiments of the present invention. In general, as used herein, the term "alkaline stabilized sludge" is intended to encompass at least products made by mixing wastewater sludge with at least one material selected from a group including lime, cement kiln dust, lime kiln dust, and coal combustion ashes to form a mixture. The amount of the added material mixed with the sludge is sufficient to raise the pH of the mixture to 12 and above for at least one day, and the mixture is dried. The end product is a granular material, and the amount of added material mixed with the sludge and the length of time of drying is sufficient to reduce the significantly-offensive odor of the sludge to a tolerable level, to reduce animal viruses therein to less than one plaque-forming unit per 100 ml of the sludge, to reduce pathogenic bacteria therein to less than three colony-forming units per 100 ml of the sludge, to reduce parasites therein to less than one viable egg per 100 ml of the sludge, to reduce vector attraction to the sludge, and to prevent significant regrowth of pathogenic microorganisms.

The term "alkaline stabilized sludge" is further intended to encompass products made by mixing waste sludge (including, but not limited to, sludges from wastewater treatment plants) and alkaline materials to form a mixture wherein the amount of alkaline materials is sufficient to raise the pH of the mixture to at least 12 and to maintain that pH for at least 12 hours, raising the temperature of the mixture to at least 50° C. for 12 hours, during which time the pH remains at 12 or above, and drying the mixture to achieve a final solids content of at least 50%.

The experiments described below demonstrated the effectiveness of embodiments of the present invention in controlling plant nematodes.

I. Methods

A. Pot Incubations

The impact of alkaline-stabilized sludge on SCN root infection was assessed in pot experiments. Pasteurized masonry sand was treated with amendments by mixing the material into a bulk soil sample, in accordance with the experimental protocols set forth in Table 1 below. Each treated soil was dispensed into a series of ten replicate 4-inch plastic pots, and each pot was then immediately inoculated with a uniform number of SCN cysts (100, inoculum obtained from SCN-infested soybean pot enrichments) which were then mixed into the soil. Pots were placed in a temperature-controlled plant growth chamber set at the following conditions: 60% humidity; 18 h/6 h light/dark cycle; 22° C. during light/18° C. during dark. Soil was kept moist by periodic addition of distilled water. After 1 week of incubation, each pot was planted with 4 soybeans of a susceptible variety (i.e., Elgin 87). All pots received 5 mls of aqueous 20-20-20 N-P-K to normalize fertility 1 week following germination of soybeans. Forty-two days post-planting, incubations were terminated and roots were separated from soil. The recovered soil was evaluated for soil cyst and egg populations, and the roots were evaluated for infection as described below.

TABLE 1

Treatment Application Protocols for Pot Incubations

| | | Tons/acre Equivalent† | | |
| Treatment | lime-kiln SS | fly ash SS | calcite | cysts |
| --- | --- | --- | --- | --- |
| 1 | – | – | – | + |
| 2 | +5 | – | – | + |
| 3 | – | +5 | – | + |
| 4 | – | – | +2 | + |
| 5 | – | – | – | – |

†Rate corresponds to liming equivalent of 5 t/ac alkaline-stabilized sludge, estimating 40% liming ability.

B. Tube Incubations

The impact of alkaline-stabilized sludge on SCN egg viability was also assessed in tube incubations. Kiln-dust alkaline-stabilized sludge was incorporated into pasteurized masonry sand according to the protocol specified in Table 2 below. Thus, 50 g samples were dispensed into ten replicate 100 ml (25 mm×150 mm) glass tubes per treatment. Each tube received 10 cysts which were then uniformly mixed in. Tubes were lightly capped and incubated for 1 week in a growth chamber under the same conditions as those for the pot experiments, maintaining moisture by periodic addition of water as required. At the end of the incubation period, cysts were recovered by flotation and the hatching frequency of eggs was established as described below.

TABLE 3

Treatment Application Protocols

| | | Gram/pot† | |
| Treatment | fly ash SS | calcite | cysts |
| --- | --- | --- | --- |
| 1 | – | – | – |
| 2 | +3 | – | – |
| 3 | – | +3 | – |
| 4 | – | – | +1.2 |
| 5 | – | – | – |

†Rate corresponds to liming equivalent of 5 t/ac alkaline-stabilized sludge, estimating 40% liming ability.

C. Microplot Incubations

The field efficacy of alkaline-stabilized sludge on SCN root infection was assessed in microplot experiments. Microplots were evaluated for three years and consisted of 5 treatments applied in 1996 only, at moisture adjusted rates as indicated in Table 3 below. Each treatment was replicated eight times with plots located in a field that averaged over 150 cysts/100 g of soil. Plot treatments were 2.4 m×4.0 m with four rows of susceptible Elgin 87 planted in 60 cm row spacings each year. In the first year of the study (i.e., 1996) all treatments were manually broadcast uniformly over the entire plot area, then roto-tilled to a depth of about five centimeters. Fertilizer was applied initially to field production recommendations with 150 kg/ha of muriate of potash. Herbicides were applied annually for standard broadleaf weed and grass controls, Dual (Metolachlor) at 1.8 kg active ingredient/ha, Pursuit (Imazethapyr) at 0.0375 active ingredient/ha, and Basagran Forte (Bentazon) at 0.7 active ingredient/ha. Roots were evaluated by digging out 4 roots/plot from the middle 2 rows (2 plants/row), placing them in plastic bags that were then returned to the lab, and soaking the roots for 2 hours in water at room temperature. Plant stems were cut off at the area where the roots became white. Roots were placed in flasks (250 ml wide mouth), about 100 ml water was added, and the suspended roots were agitated on a mechanical shaker for 2–4 hours. The released cysts were then screened through 25 mm screen with 60 mm screen on the bottom to catch the cysts. Roots were oven dried and weighed. Plant heights and harvesting were carried out each year in mid- to late-October.

TABLE 3

Treatment Application Protocols for Microplot Incubations

| Treatment | Material | Rate | Dry weight/plot | Wet weight/plot |
| --- | --- | --- | --- | --- |
| 1 | none | 0 | 0 | 0 |
| 2 | N-Viro Soil[1] | 5 tons/acre | 5.6 | 7.6 |
| 3 | Calcite (CaCO$_3$) | 2 t/ac | 2.24 | 2.3 |
| 4 | Windsor sludge | 5 t/ac | 5.6 | 8.9 |
| 5 | Compost | 5 t/ac | 5.6 | 12.5 |

[1]N-Viro Soil is an alkaline-stabilized sludge made from proprietary technology owned by N-Viro Energy Systems Ltd. of Toledo, Ohio.

II. Measurements

Soil sampling was carried out each year before planting and at harvest. In 1996 an additional sampling after treatments were roto-tilled was carried out.

A. Soil Cyst and Egg Population Counts

Soil SCN cyst counts were determined by slurrying soil samples in water, recovering the floating cysts by passing the supernatant over a sieve (210 μm mesh size) and counting their number under a magnifying glass. Egg counts were determined by crushing the recovered cysts in distilled water, and counting eggs in the resulting suspension with a low-power microscope.

B. Root Cyst and Egg Population Counts

Cysts were sheared off and recovered from roots by carefully sliding the roots between the ball of thumb and forefinger. Cysts were re-suspended in distilled water and cyst and egg counts done as described above.

C. Viability of SCN Eggs

Hatching of SCN eggs was taken to be a measure of viability. Cysts were re-suspended in 3 mM $ZnSO_4$ (a hatching stimulant), mechanically broken, and the resulting egg suspension distributed in the wells of a 96-well microtiter plate. Two hundred and fifty microliters of the suspension recovered from each tube was distributed into six replicate wells of a plastic 96-well microtiter plate to give approximately 24 eggs per well. Plates were incubated at room temperature. At the start of the incubation and at periodic intervals thereafter, each well was examined microscopically to count the number of eggs and the number of hatched nematodes.

D. Root Dry Weights

Root biomass was determined gravimetrically on material dried overnight at 85° C.

III. Data Handling

Statistically-significant treatment effects were evaluated with a one-way ANOVA using the student-t test.

IV. Results

A. Effect of Alkaline-Stabilized Sludge on SCN Infection of Soybean Roots

In laboratory-scale experiments, alkaline-stabilized sludge significantly reduced the degree of infection of soybeans by SCN as evidenced by the number of cysts and eggs recovered from roots (see Table 4, below). This is particularly clear when the numbers are adjusted for root mass.

In microplot experiments, the effect of alkaline-stabilized sludge on root infection was variable. In the third year of a three-year experiment, there was reduction in root infection, suggesting that there was significant long-term activity of the material or that some curing process over that time enhanced its activity.

B. Effect of Alkaline-Stabilized Sludge on Numbers of SCN Cysts and Eggs in Soil In both lab and field incubations there was no detectable significant declines in soil counts of cysts or eggs (see Table 4).

C. Effect of Alkaline-Stabilized Sludge on Viability of SCN Eggs

The viability of eggs recovered from treated soils was assessed on the basis of their ability to hatch when re-suspended in a suitable buffer. Eggs recovered from three soils treated with alkaline-stabilized sludge generally hatched at equivalent or faster rates when compared to eggs recovered from untreated control soils (see Table 4). In one loam soil, eggs from soil treated at a higher rate of alkaline-stabilized sludge addition appeared to hatch less rapidly, suggesting that there is some soil-dependent variability.

Alkaline-stabilized sludge reduced the rate of infection of soybean roots by SCN when it was added to SCN-infested soil at agronomically-reasonable rates (see Table 1). The effect was observed with sewage sludge stabilized either with cement kiln dust or with fly ash, and at a range of application rates.

On the basis of soil cyst and egg counts, and the hatching frequency of recovered eggs, alkaline-stabilized sludge was not found to be nematocidal at application rates which reduce root infection. The mechanism of infection suppression is therefore not strictly a reduction in viable soil SCN populations. However, without being bound by theory, the following mechanism(s) may be responsible for the observed reduction in root infection:

1. The alkaline-stabilized sludge acts on the nematode directly, or interferes with the infection-promoting chemical signaling between plant root and nematode, such that the nematode does not initiate or follow through with the infection process. This interference could be through inhibition of egg hatching, movement towards the root, or expression of other functions or behavior by the nematode required for root penetration and subsequent steps in the infection cycle.

2. The alkaline-stabilized sludge influences the plant in order to make it less amenable to infection by SCN—a form of induced resistance. This could be due to modification of the composition of root exudates to reduce their ability to promote SCN pathogenic behavior, modification of root architecture or surface properties such that it is less vulnerable to infection, or modification of the root physiology such that it eliminates or inhibits the nematode once it has entered the root.

3. The alkaline-stabilized sludge influences the microbial composition of the soil such that microbial activities which promote the infection process are reduced, and/or microbial activities which inhibit the infection process are enhanced. This could be due to microbial production of compounds which act on either the nematode or the soybean host to inhibit infection by any of the mechanisms outlined above, microbial degradation of infection-promoting compounds in root exudates, or an effect on soybean symbiotic partners such as rhizobia or mycorrhiza which, through their association with soybean roots, alter the plant's physiology to inhibit infection via any of the mechanisms outlined above.

D. Effect of Alkaline-Stabilized Sludge on SCN Infection of Soybean Roots (repeat experiment)

This experiment studied the impact of alkaline-stabilized sludge on numbers of SCN cysts and eggs in soil and the degree of root infection, as evidenced by numbers of eggs and cysts per gram dry root mass. These results are also shown in Table 4 below.

TABLE 4

| Treatment | Addition | Cysts from Soil | | Eggs in soil cysts | | Cysts/gr dry root | | Egg/gr dry root | |
|---|---|---|---|---|---|---|---|---|---|
| | | Mean | S.D. | Mean | S.D. | Mean | S.D. | Mean | S.D. |
| 1 | None | 50 | 12 | 6609 | 1239 | 61 | 38 | 14465 | 15425 |
| 2 | Lime-kiln | 43 | 10 | 2446 | 196 | 13 | 15 | 2272 | 2176 |
| 3 | Fly ash | 57 | 13 | 16245 | 989 | 14 | 12 | 3340 | 4176 |
| 4 | Calcite | 47 | 15 | 7662 | 3148 | 59 | 26 | 16270 | 10188 |

E. Effect of Alkaline-Stabilized Sludge on Viability of SCN Eggs

This experiment studied the effect of alkaline-stabilized sludge on the viability of SCN eggs recovered from three soils. Eggs were re-suspended in a hatching-promoting buffer, and the percentage of eggs hatching over time was determined. Lime kiln dust-treated sewage sludge was used. The results are shown in Table 5 below.

TABLE 5

| Treatment | Soil | Rate (g/kg) | Day 0 % Hatched Mean | Day 0 % Hatched S.D. | Day 5 % Hatched Mean | Day 5 % Hatched S.D. | Day 12 % Hatched Mean | Day 12 % Hatched S.D. | Day 15 % Hatched Mean | Day 15 % Hatched S.D. |
|---|---|---|---|---|---|---|---|---|---|---|
| 1 | sand | 1 | 4.86 | 0.88 | 17.49 | 4.28 | 42.76 | 7.65 | 45.9 | 7.59 |
| 2 | | 0.1 | 3.96 | 1.36 | 21.47 | 4.03 | 39.3 | 5.01 | 40.59 | 4.671 |
| 3 | | 0.01 | 3.59 | 1.64 | 34.02 | 10.23 | 44.2 | 2.24 | 45.6 | 0.68 |
| 4 | | none | 2.86 | 0.96 | 14.85 | 6.33 | 30.28 | 3 | 30.82 | 4.08 |
| 5 | clay | 1 | 3.43 | 2.23 | 8.97 | 2.76 | 27.19 | 8.06 | 31.64 | 7.21 |
| 6 | | 0.1 | 6.51 | 2.48 | 20.01 | 5.65 | 43.46 | 8.06 | 44.83 | 7.6 |
| 7 | | 0.01 | 4.34 | 1.13 | 17.71 | 3.71 | 31.4 | 6.33 | 32.86 | 5.72 |
| 8 | | none | 8.26 | 2.78 | 17.72 | 3.85 | 21.53 | 5.17 | 22.02 | 5.29 |
| 9 | loam | 1 | 2.18 | 0.48 | 5.41 | 3.01 | 8.43 | 3.98 | 9.7 | 2.89 |
| 10 | | 0.1 | 3.49 | 1.42 | 6.05 | 3.05 | 9.43 | 4.5 | 11.01 | 5.02 |
| 11 | | 0.01 | 0 | 0 | 0 | 0 | 15.66 | 3.16 | 24.77 | 2.82 |

The foregoing is a detailed description of particular embodiments of the present invention. The invention embraces all alternatives, modifications and variations that fall within the letter and spirit of the claims, as well as all equivalents of the claimed subject matter.

What is claimed:

1. A method for controlling plant-parasitic nematodes, comprising applying an effective amount of an alkaline-stabilized wastewater sludge to at least one of a plant host, a seed of a plant host, or a locus of a plant host, wherein said alkaline-stabilized wastewater sludge comprises a granular product made by mixing a quantity of wastewater sludge with a quantity of an alkaline material and drying the mixture for a period of time, wherein the quantity of alkaline material is sufficient to raise a pH level of the mixture to at least 12 for a period of at least 24 hours, and wherein the quantity of alkaline material and said drying are sufficient to reduce offensive odors associated with waste sludge to a tolerable level, to reduce animal viruses in the mixture to less than one plaque-forming unit per 100 ml, to reduce pathogenic bacteria in the mixture to less than three colony-forming units per 100 ml, and to reduce parasites in the mixture to less than one viable egg per 100 ml.

2. A method for controlling plant-parasitic nematodes, comprising applying an effective amount of an alkaline-stabilized wastewater sludge to at least one of a plant host, a seed of a plant hosts, or a locus of plant host, wherein said alkaline-stabilized wastewater sludge comprises a granular product made by mixing a quantity of waste sludge with a quantity of an alkaline material and drying the mixture, wherein the quantity of alkaline material is sufficient to raise pH level of the mixture to at least 12 and to raise a temperature of the mixture to at least 50° C., and maintain said conditions for a period of at least approximately 12 hours, and wherein the mixture is dried for a period of time sufficient to achieve a solids content of at least approximately 50%.

3. The method of claim 1 or 2 , wherein said alkaline-stabilized wastewater sludge is applied using at least one technique selected from a group consisting of broadcast incorporation and side dressing.

4. The method of claim 1 or 2, wherein said method is used to control plant-parasitic nematodes selected from at least one of the genus Heterodera, Pratylinchus, and Meloidogyne.

5. The method of claim 3, wherein said plant-parasitic nematode is *Heterodera glycine*.

6. The method of claim 5, wherein the plant host is a soybean plant.

7. The method of claim 1 or 2, wherein the effective amount of alkaline-stabilized wastewater sludge comprises an amount resulting from an application rate between approximately 5 tons per acre and approximately 10 tons per acre.

* * * * *